(12) United States Patent
Moreno et al.

(10) Patent No.: US 11,364,104 B2
(45) Date of Patent: *Jun. 21, 2022

(54) HETEROGENEOUS INSEMINATE SYSTEM

(71) Applicant: XY, LLC, Navasota, TX (US)

(72) Inventors: Juan F. Moreno, Navasota, TX (US); Maurice A. Rosenstein, Navasota, TX (US)

(73) Assignee: XY, LLC, Navasota, TX (US)

( * ) Notice: Subject to any disclaimer, the term of this patent is extended or adjusted under 35 U.S.C. 154(b) by 146 days.

This patent is subject to a terminal disclaimer.

(21) Appl. No.: 16/693,075

(22) Filed: Nov. 22, 2019

(65) Prior Publication Data

US 2020/0121436 A1 Apr. 23, 2020

Related U.S. Application Data

(63) Continuation of application No. 15/332,123, filed on Oct. 24, 2016, now Pat. No. 10,492,896, which is a continuation of application No. 13/702,986, filed as application No. PCT/US2011/001052 on Jun. 8, 2011, now Pat. No. 9,474,591.

(60) Provisional application No. 61/353,140, filed on Jun. 9, 2010.

(51) Int. Cl.

| A61D 19/02 | (2006.01) |
| A61D 19/00 | (2006.01) |
| C12N 5/076 | (2010.01) |
| A61B 17/43 | (2006.01) |

(52) U.S. Cl.
CPC .............. *A61D 19/02* (2013.01); *A61B 17/43* (2013.01); *A61D 19/00* (2013.01); *C12N 5/061* (2013.01)

(58) Field of Classification Search
CPC ........ A61D 19/02; A61D 19/00; A61B 17/43; C12N 5/061
USPC ................... 600/33–35; 435/2; 128/897–899
See application file for complete search history.

(56) References Cited

U.S. PATENT DOCUMENTS

| 4,267,268 A | 5/1981 | Nelson, Jr. |
| 4,362,246 A | 12/1982 | Adair |
| 5,135,759 A | 8/1992 | Johnson |
| 5,474,890 A | 12/1995 | Di Virgilio et al. |
| 5,569,581 A | 10/1996 | Killian et al. |

(Continued)

FOREIGN PATENT DOCUMENTS

| CN | 1732983 | 2/2006 |
| CN | 1927226 | 3/2007 |

(Continued)

OTHER PUBLICATIONS

Batellier et al. Delayed insemination is successful with a new extender for storing fresh equine semen at 15 degrees C under aerobic conditions. Theriogenology, Jul. 1998, 15:50(2):229-36.

(Continued)

*Primary Examiner* — Sunita Reddy
(74) *Attorney, Agent, or Firm* — Craig R. Miles; CR Miles P.C.

(57) ABSTRACT

A first amount of sperm of a first animal and a second amount of sperm of a second animal of the same species, the first amount of sperm and the second amount of sperm sex-selected sperm of the same sex, useful in the in-vivo or in-vitro fertilization of an egg of a female animal of the same species of animal for the production of sex-selected embryos and sex-selected offspring.

16 Claims, 6 Drawing Sheets

(56) References Cited

U.S. PATENT DOCUMENTS

| | | | |
|---|---|---|---|
| 5,770,363 | A | 6/1998 | Brown |
| 5,972,592 | A | 10/1999 | Suarez |
| 6,042,025 | A | 3/2000 | Crampton et al. |
| 6,372,422 | B1 | 4/2002 | Seidel et al. |
| 7,024,316 | B1 | 4/2006 | Ellison et al. |
| 7,070,917 | B1 | 7/2006 | Christensen et al. |
| 7,071,917 | B2 | 7/2006 | Kori |
| 7,169,548 | B2 | 1/2007 | Maxwell et al. |
| 7,195,920 | B2 | 3/2007 | Seidel et al. |
| 7,371,517 | B2 | 5/2008 | Evans et al. |
| 7,723,116 | B2 | 5/2010 | Evans et al. |
| 7,758,811 | B2 | 7/2010 | Durack et al. |
| 7,943,384 | B2 | 5/2011 | Durack et al. |
| 8,251,887 | B2 | 8/2012 | Li et al. |
| 9,474,591 | B2 | 10/2016 | Moreno et al. |
| 10,492,896 | B2 | 12/2019 | Moreno et al. |
| 2002/0119558 | A1* | 8/2002 | Seidel .................. C12N 5/0612 435/287.1 |
| 2004/0055030 | A1* | 3/2004 | Maxwell .............. C12N 5/0604 800/21 |
| 2005/0053910 | A1 | 3/2005 | McKenzie et al. |
| 2006/0121440 | A1 | 6/2006 | Schenk et al. |
| 2010/0191042 | A1 | 7/2010 | Li et al. |

FOREIGN PATENT DOCUMENTS

| | | |
|---|---|---|
| CN | 101220345 | 7/2008 |
| JP | 2008-63235 | 3/2008 |
| WO | WO/2010/045758 | 4/2010 |

OTHER PUBLICATIONS

Buchanan et al. Insemination of mares with low numbers of either unsexed or sexed spermatozoa. Theriogenology, Apr. 2000, 53(6):1333-1344.

Johnson. Sex preselection by flow cytometric separation of X and Y chromosome-bearing sperm based on DNA difference: a review. Reprod Fertil Dev. 1995; 7(4):893-903.

Province et al. Cooling rates, storage temperatures and fertility of extended equine spermatozoa. Theriogenology, Jun. 1985, 23(6):925-934.

Tardif et al. Use of Hoechst 33342 stain to evaluate live fresh and frozen bull sperm by computer-assisted analysis. J Androl. Mar.-Apr. 1998; 19(2):201-6.

Cooper et al. Infertility in a Hereford bull associated with increased numbers of detached sperm heads in his ejaculate. Australian Veterinary Journal, Jul. 1983, vol. 60, No. 7, pp. 225-226.

Friedman. Artificial Insemination with Donor Semen Mixed with Semen of the Infertile Husband. Fertility and Sterility, vol. 33, Issue 2, Feb. 1940. pp. 125-128. (Year: 1980).

Takahashi et al. Archiving and Distributing Mouse Lines by Sperm Cry opreservation, IVF, and Embryo Transfer. Methods Enzymol. 2010, 476:53-69.

Tomlinson et al. Validation of a novel computer-assisted sperm analysis (CASA) system using multitarget-tracking algorithms. Fertility and Sterility, Apr. 2010, vol. 93, No. 6, pp. 1911-1920.

Corresponding Canadian Patent Application No. 2,800,408; Office Action dated Dec. 7, 2015; 4 pages total.

Corresponding Canadian Patent Application No. 2,800,408; Notice of Allowance dated Jun. 14, 2016; 1 page.

Corresponding Canadian Patent Application No. 2,800,408; Office Action dated Mar. 13, 2017; 3 pages total.

U.S. Appl. No. 13/702,986; Office Action dated Mar. 12, 2014.
U.S. Appl. No. 13/702,986; Office Action dated Jan. 2, 2015.
U.S. Appl. No. 13/702,986; Office Action dated Jul. 31, 2015.
U.S. Appl. No. 13/702,986; Office Action dated Sep. 21, 2015.
U.S. Appl. No. 13/702,986; Office Action dated Mar. 23, 2016.
U.S. Appl. No. 15/332,123; Office Action dated Oct. 23, 2018.
U.S. Appl. No. 15/332,123; Office Action dated May 16, 2019.

Corresponding Brazilian Patent Application No. BR1120120313851; Office Action dated Mar. 11, 2020.; 4 pages total.

International Patent Cooperation Treaty Patent Application No. PCT/US2011/001052, filed Jun. 8, 2011.

U.S. Appl. No. 61/353,140, filed Jun. 9, 2010.
U.S. Appl. No. 13/185,400, filed Jul. 18, 2011.
U.S. Appl. No. 12/806,945, filed Aug. 24, 2010.
U.S. Appl. No. 10/523,268, filed Jul. 7, 2005.

International Patent Cooperation Treaty Patent Application No. PCT/US2003/024460, filed Aug. 1, 2003.

U.S. Appl. No. 60/400,971, filed Aug. 1, 2002.
U.S. Appl. No. 13/185,400; Office Action dated Oct. 16, 2012.

Azmal et al. Relative merits of homo and heterospermic bull semen in respect of preservation quality. Pakistan Journal of Biol. Sci., vol. 7, pp. 1908-1911, Nov. 2004.

Beatty. A Pilot Experiment with Heterospermic Insemination in the Rabbit. J Genetics vol. 55, No. 2, pp. 325-347, 1957; abstract.

Beatty. Fertility of mixed semen from different rabbits. Journal or Reprod. Fertil. vol. 1, pp. 52-60, Feb. 1960.

Elliott. Heterospermic Trials at A.B.S. Proceedings of the 5th Technical Conference on Artificial Insemination and Reproduction, 1974.

Flint, et al. Fertility Assessment through Heterospermic Insemination of Flow-Sorted Sperm in Cattle, J Anim Sci, 81, 1814-1822, 2003.

Johnson et al. Sex Preselection: High-Speed Flow Cytometric Sorting of X and Y Sperm for Maximum Efficiency. Theriogenology, vol. 52, pp. 1323-1341, 1999.

Rath, et al. In Vitro Production of Sexed Embryos for Gender Precelection: High-Speed Sorting of X-Chromosome-Bearing Sperm to Produce Pigs After Embryo Transfer. J Anim Sci 77:3346-3352, 1999.

Stahlberg, et al. Identification of Embryo Paternity Using Polymorphic DNA Markers to Assess Fertilizing Capacity of Spermatozoa After Heterospermic Insemination in Boars. Theriogenology 53:1365-1373, 2000.

Yassen, et al. Freezability of Bovine Spermatozoa in Tris-Buffered Yolk Extenders Containing Different Levels of Tris, Sodium, Potassium and Calcium Ions. Dairy Science, vol. 50, No. 6, pp. 887-892, 1966.

Beatty. A Pilot Experiment with Heterospermic Insemination in the Rabbit. J Genetics vol. 55, No. 2, pp. 325-347, 1957.

U.S. Appl. No. 13/702,986, filed Dec. 7, 2012.

Corresponding Canadian patent application No. 2,800,408; Office Action dated Feb. 3, 2015, 4 total pages.

Corresponding EP Patent Application No. 11792787.1; OA dated Mar. 12, 2014, 6 total pages.

Corresponding NZ Patent Application No. 629047; OA mailed Sep. 9, 2012, 2 total pages.

Baccetti et al. Infertile spermatozoa in a human carrier of robertsonian translocation 14;22. Fertility and Sterility, Nov. 2002, vol. 78, No. 5, pp. 1127-1130.

Beef Semen Online. High Fertility Semen. Website, http:///www.beefsemenonline.co.uk, originally downloaded Mar. 11, 2009, 1 total page, United Kingdom.

Foote. Buffers and Extenders: What Do They Do? Why Are They Important? Proc of the 10th NAAB Tech. Conf. On Artificial Insemination and Reproduction, 1984, pp. 62-70.

Foote. The history of artificial insemination: Selected notes and notables. Journal of Animal Science, Jan. 2002, 80(1):1-10.

Garner et al. Seminal plasma addition attenuates the dilution effect in bovine sperm. Theriogenology, Jul. 2001, 56:31-40.

Fugger et al. Births on normal daughters after MicroSort sperm separation and intrauterine insemination, in-vitro fertilization, or intracytoplasmic sperm injection; Human Reproduction, Sep. 1998, vol. 13, No. 9, pp. 2367-2370.

Heterogeneous; Definition. Merriam-Webster Dictionary, http://www.merriam-webster.com, originally downloaded Jun. 14, 2012, 1 total page.

Kaeoket et al. A preliminary study on using autologous and heterologous boar sperm supernatant from freezing processes as post-thawing solution: its effect on sperm motility. Trop Anim Health Prod, Feb. 2011, 43:1049-1055.

(56) References Cited

OTHER PUBLICATIONS

Li et al. Research Advance of Technology of Bull Semen Cryopreservation. China Cattle Science, Sep. 2006, vol. 32, No. 5, pp. 59-62, p. 66 (abstract), China.

Moussa et al. Low density lipoproteins extracted from hen egg yolk by an easy method: cryoprotective effect on frozen-thawed bull semen. Theriogenology, Apr. 2002, vol. 57, pp. 1695-1706.

Napier. Fertility in the male rabbit. J. Reprod. Fertil., Aug. 1961, vol. 2, No. 3, pp. 273-289.

Parks et al. Cryopreservation of peregrine falcon semen and post-thaw dialysis to remove glycerol. Raptor Research, 1986, 20(1), pp. 15-20.

Perez-Garnelo et al. Post-thaw viability of European bison (*Bison bonasus*) semen frozen with extenders containing egg yolk or lipids of plant origin and examined with a heterologous in vitro fertilization assay. Journal of Zoo and Wildlife Medicine, Jun. 2006, vol. 37, Issue 2, pp. 116-125.

Roth et al. Scimitar-Horned Oryx (*Oryx dammah*) Spermatozoa Are Functionally Competent in a Heterologous Bovine In Vitro Fertilization after Cryopreservation on Dry Ice, in a Dry Shipper, or over Liquid Nitrogen Vapor. Biology of Reproduction, Feb. 1999, 60(2), pp. 493-498.

Ryder. Genus mixed-semen service increases conception rates. Farmers Guardian, Jan. 2003, 2 total pages, United Kingdom.

Suquet et al. Cryopreservation of sperm in marine fish. Aquaculture Research, Mar. 2000, 31(1), pp. 231-243.

Tartaglione et al. Prognostic value of spermatological parameters as predictors of in vitro fertility of frozen-thawed bull semen. Theriogenology, Oct. 2004, 62(7), pp. 1245-1252.

Tiersch. Strategies for commercialization of cryptopreserved fish semen. Revista Brasileira de Zootecnia, 2008, v. 37, Suplemento especial pp. 15-19, Brazil.

Wang et al. Study on application of frozen sexed X-semen of dairy cow AI. Journal of Guangxi Agric. and Biol. Science, Sep. 2006, vol. 25, pp. 191-192.

Vogt et al. Human Y chromosome azoospermia factors (AZF) mapped to different subregions in Yq11. Human Molecular Genetics, 1996, vol. 5, No. 7, pp. 933-943, Oxford University Press.

\* cited by examiner

PRIOR ART

HETEROGENEOUS INSEMINATE SYSTEM

This United States Patent Application is a continuation of U.S. patent application Ser. No. 15/332,123, filed Oct. 24, 2016, now U.S. Pat. No. 10,492,896, issued Dec. 3, 2019, which is a continuation of U.S. patent application Ser. No. 13/702,986, filed Dec. 7, 2012, now U.S. Pat. No. 9,474,591, issued Oct. 25, 2016, which is the United States National Stage of International Patent Cooperation Treaty Patent Application No. PCT/US2011/001052, filed Jun. 8, 2011, which claims the benefit of U.S. Provisional Patent Application No. 61/353,140, filed Jun. 9, 2010, each hereby incorporated by reference herein.

I. BACKGROUND

Artificial insemination of female animals and in-vitro fertilization of oocytes with fresh or frozen-thawed semen have been applied to the reproduction of animals. According to the traditional theory and conventional procedures, a great number of sperm cells are needed to ensure a successful fertilization.

However, semen from certain animals and sex-selected sperm which are produced by separating X-chromosome bearing sperm cells from Y-chromosome bearing sperm cells into distinct subpopulations may be available only in limited supply. Additionally, the sperm of certain animals and sex-selected sperm can have reduced fertility or cannot achieve the threshold of fertility in the context of conventional procedures for successful fertilization of eggs whether in-vitro or in-vivo.

Additionally, cryopreservation and thawing of semen and sex-selected sperm can result in substantially reduced motility, percent intact acrosomes and post thaw survival time, all of which can militate against successful use of cryopreserved-thawed sperm for the in-vitro or in-vivo fertilization of eggs of the same species of animal.

Additionally, certain animals, such as dairy cows, are known to have reduced fertility as compared to heifers. An adverse side effect of acquiring certain genetic traits advantageous to milk production can be concurrent with acquisition of genetic traits which lower fertility of dairy cows. Moreover, as to the example of dairy cows, it may also be desirable to increase the proportion of female offspring by the use of sex-selected sperm. In order to successfully breed animals having reduced fertility, especially in the instance of utilizing sex-selected sperm to increase the number of female offspring, it would be useful to have an inseminate, and a method of producing such inseminate, having increased fertility in order to increase pregnancy rates.

Therefore, a need exists for a method of increasing fertility of sperm within an inseminate to overcome reduced fertility in inseminates whether due to low numbers of sperm contained in the inseminate, low fertility of sperm relating to animal to animal variation, the process of sex-selection, the low fertility of the female animal, or the like.

II. SUMMARY OF THE INVENTION

Accordingly, a broad object of the invention can be to provide a heterogeneous inseminate in which a first amount of sperm and a second amount of sperm obtained from a corresponding first animal and a second animal are combined resulting in an increase in the fertility of at least one of the first amount of sperm or the second amount of sperm such that the eggs of an animal can be fertilized whether by in-vitro or in-vivo insemination with increased success rates as compared with conventional inseminates containing the sperm of only one animal.

Another broad object of the invention can be to provide a heterogeneous inseminate in which a first amount of sperm and a second amount of sperm obtained from a corresponding first animal and a second animal are combined, the second amount of sperm containing substantially fewer sperm than the first amount of sperm, resulting in an increase in fertility in the second amount of sperm such that the eggs of an animal can be fertilized whether in-vitro or in-vivo by one of the sperm of the second amount of sperm with increased success rates as compared to conventional inseminates containing only a reduced number of sperm of the second animal, thereby increasing the number of embryos produced per unit of a rare genetic resource and can reduce the cost of embryo production.

Another broad object of the invention can be to provide a heterogeneous inseminate in which a first amount of sperm and a second amount of sperm obtained from a corresponding first animal and a second animal are combined, the first or the second amount of sperm or both being sex-selected sperm, resulting in an increase in fertility of the first or second amount of sex-selected sperm resulting in an increase in fertility in the first or the second amount of sex-selected sperm or both such that the eggs of an animal can be fertilized whether in-vitro or in-vivo by one of the sperm of the first or second amount of sex-selected sperm with increased success rates as compared to conventional inseminates containing only sex-selected sperm of only one animal, thereby increasing the number of embryos produced per unit of sex-selected sperm and can reduce the cost of embryo production.

Another broad object of the invention can provide a cryopreserved heterogeneous inseminate in which a first amount of sperm and a second amount of sperm obtained from a corresponding first animal and a second animal are combined, the first or the second amount of sperm or both being sex-selected sperm, resulting in an increase in fertility of the first or second amount of sex-selected sperm upon being thawed resulting in an increase in fertility in the first or the second amount of sex-selected sperm or both such that the eggs of an animal can be fertilized whether in-vitro or in-vivo by one of the sperm of the first or second amount of sex-selected sperm with increased success rates as compared to conventional cryopreserved inseminates containing sex-selected sperm of only one animal, thereby increasing the number of embryos produced per unit of sex-selected sperm and can reduce the cost of embryo production.

Naturally, further objects of the invention are disclosed throughout other areas of the specification, drawings, photographs, and claims.

III. BRIEF DESCRIPTION OF THE DRAWINGS

IV. MODE(S) FOR CARRYING OUT THE INVENTION

Figure 1:
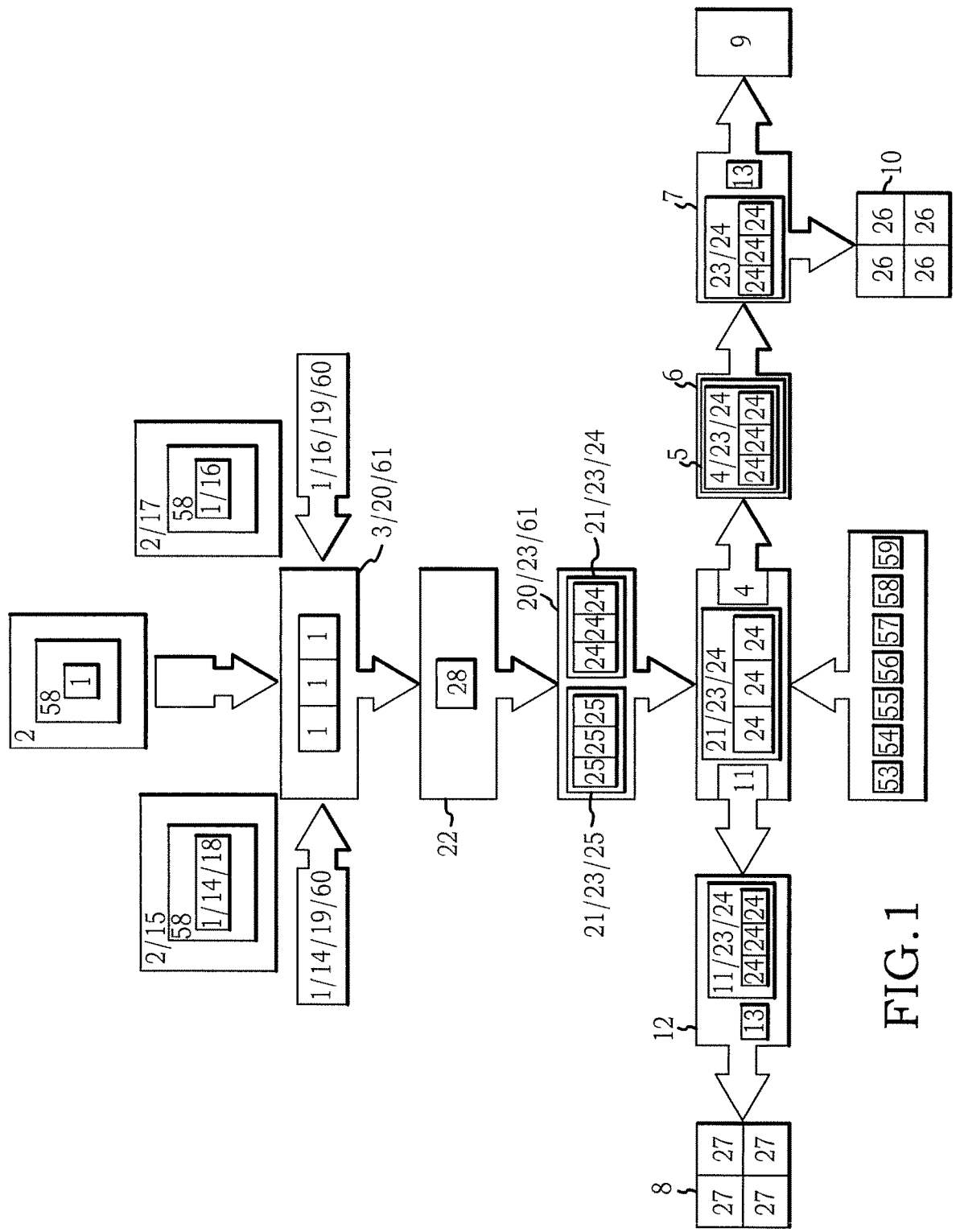
FIG. 1 is a block diagram which shows a particular method of how to make and use an embodiment of the inventive heterogeneous inseminate.

Generally, a heterogeneous inseminate produced by combining a first amount of sperm obtained from a first animal with a second amount of sperm of a second animal of the same species useful in the in-vitro or in-vivo fertilization of an egg of a female animal of the species for the production embryos and offspring. Specifically, a first amount of sperm of a first animal and a second amount of sperm of a second animal of the same species, the first amount of sperm and the second amount of sperm sex-selected sperm of the same sex, useful in the in-vivo or in-vitro fertilization of an egg of a female animal of the same species of animal for the production of sex-selected embryos and sex-selected offspring.

For the purposes of this invention, the term "animal" means a species of mammal, ayes, or fish from which semen containing an amount of sperm is produced by a male animal of the species and an egg is produced by the female animal of the species and a mammal, without limiting the general forgoing statement, can be a species of: horse, cattle, camel, deer, pig, sheep, goat, dog, cat, lion, whale, dolphin, porpoise, seal, hare, rabbit, elephant, mouse, rat, or the like, and a fish, without limiting the general forgoing statement, can be a species of: salmon, tuna, sturgeon, halibut, catfish, or the like, and a bird, without limiting the general forgoing statement can be a species of: chicken, turkey, eagle, falcon, ostrich, emu, duck, goose, or the like.

For the purposes of this invention the term "semen" means seminal fluid which may contain sperm (also referred to as "spermatozoa") secreted by the gonads of a male animal which can be collected from the male animal by a variety of methods such as use of an artificial vagina, manual manipulation of the penis, electrical manipulation of the anus, or the like.

For the purposes of this invention the term "sperm" means the haploid cell that is the gamete of a male animal which may join an egg (also referred to as "ovum") to produce a zygote and broadly encompasses infertile sperm, sperm having a comparably lesser or a comparably greater fertility between a first amount of sperm obtained from a first animal and a second amount of sperm obtained from a second animal and which may be obtained in the form of a raw ejaculated semen, frozen semen, as sperm separated from the semen and contained in an extender or diluent, or as sex-selected sperm.

For the purposes of this invention the term "sex-selected sperm" means sperm which have been separated, regardless as to the method of separation, into subpopulations containing X-chromosome bearing sperm and Y-chromosome bearing sperm having a purity in the range of about 70 percent ("%") and about 100%.

For the purposes of this invention, the term "inseminate" is intended to broadly encompass an amount of sperm whether contained in semen or other extender or diluent which can be utilized to fertilize the eggs of a female animal whether in-vitro or in-vivo and without limitation to the general forgoing statement can be an amount of sperm whether or not sex-selected introduced or injected into the reproductive tract of a female animal whether by artificial insemination procedures or otherwise, or utilized in in-vitro fertilization procedures.

For the purposes of this invention, the term "heterogeneous inseminate" means an inseminate in the form of a combination of a first amount sperm obtained from a first male animal and a second amount of sperm obtained from a second male animal, the first animal and the second male animal being of the same species; however, the invention is not so limited and a plurality of amounts of sperm obtained from a corresponding plurality of male animals of the same species can be combined to produce various embodiments of the heterogeneous inseminate.

For the purposes of this invention, the term "sex-selected heterogeneous inseminate" means a heterogeneous inseminate having the first amount of sperm obtained from a first male animal and the second amount of sperm obtained from a second male animal (or a plurality of amounts of sperm obtained from a plurality of animals) which are processed, whether prior to combination or after combination, such that the first amount of sperm and the second amount of sperm (or the plurality of amounts of sperm) contained in a heterogeneous inseminate are sex-selected sperm.

For the purposes of this invention, the term "fertility" means the fertilization rate determined for an artificial insemination procedure as the number of pregnancies achieved within a population of inseminated female animals divided by the total number inseminated female animals and multiplied by 100 or determined for in-vitro fertilization procedure as the number of embryos (greater than or equal to two cells) divided by the sum of the embryos and oocytes recovered and multiplied by 100.

For the purposes of this invention, the term "motility" means moving sperm in an inseminate or sample of sperm.

For the purposes of this invention, the term "infertile" means as to any particular procedure incapable of fertilizing an egg of a female animal.

Now referring to primarily to FIG. 1, a plurality of amounts of sperm cells (1) can be obtained from a corresponding plurality of male animals (2), each of the plurality of male animals (2) of the same species. The term "plurality of male animals" (2) can encompass two, three, four, five, six, or a greater number of male animals (2). The plurality of amounts of sperm cells (1) can be combined to achieve a heterogeneous inseminate (3). The heterogeneous inseminate (3) can be divided to produce a number of artificial insemination dosages (4) which can as to particular embodiments be contained one each in a corresponding number artificial insemination straws (5). One or more of the artificial insemination doses (4) can be used for artificial insemination (6) of a female animal (7) of the same species for the production of in-vivo embryos (8) whether as single embryo pregnancies to generate offspring (9) for meat or animal replacement or multiple embryo pregnancies for multiple ovulation embryo transfer ("MOET") by subsequent flushing of a plurality of in-vivo embryos (8) from the female animal (7). As to other embodiments, the heterogeneous inseminate (3) can be divided or used as a number of in-vitro fertilization doses (11) for in-vitro fertilization (12) of one or more eggs (13) obtained from a female animal (7) to produce a plurality of in-vivo (8).

Again referring primarily to FIG. 1, while a plurality of amounts of sperm (1) from a corresponding plurality of male animals (2) is shown; a particular illustrative example useful in understanding the numerous and varied embodiments of the invention can include a first amount sperm (14) obtained from a first male animal (15) and a second amount of sperm (16) obtained from a second male animal (17). The first male animal (15) and the second male animal (17) being of the same species. The first amount of sperm (14) obtained from the first male animal (15) can be combined with the second amount of sperm (16) obtained from the second male animal (17) to produce a particular embodiment of the heterogeneous inseminate (3).

As to particular embodiments of the heterogeneous inseminate (3), the first amount of sperm (14) can be an amount of infertile sperm (18) while the second amount of sperm (16) can have an initial level of fertility (19) outside of the heterogeneous inseminate (3). Upon combination of the first amount of sperm (14) (infertile sperm (18)) with the second amount of sperm (16), as concentration of the first amount of sperm (14) increases in the heterogeneous inseminate (3) as compared to the concentration of the second amount of sperm (16), the second amount of sperm (16) can exhibit by comparison to the initial level of fertility (19) an increased level of fertility (20) within the heterogeneous inseminate (3). Accordingly, the first amount sperm (14) can be sufficient in number or concentration within the heterogeneous inseminate (3) such that, the second amount of sperm (16) achieves by comparison to the initial level of fertility (19) an increased level of fertility (20).

As to other particular embodiments of the heterogeneous inseminate (3), the first amount of sperm (14) outside the heterogeneous inseminate (3) can have greater fertility than the initial level of fertility (19) of the second amount of sperm (16) outside of the heterogeneous inseminate (3). In combination, the second amount of sperm (16) can exhibit an increased level of fertility (19) within the heterogeneous inseminate (3). Accordingly, the heterogeneous inseminate (3) can afford a substantial advantage over conventional inseminates when the second amount of sperm (16) can confer desirable genetic traits but has an initial level of fertility (19) outside of the heterogeneous inseminate (3) which may be unsuitable for use as an artificial insemination dosage (4) for the artificial insemination (6) of a female animal (7) or may be unsuitable for use as an in-vitro fertilization dose (11) for in-vitro fertilization (12) of eggs (13) obtained from a female animal (7). The comparably lesser initial level of fertility (19) of the second amount of sperm (16) outside of the heterogeneous inseminate (3) as compared to increased level of fertility (20) inside of the heterogeneous inseminate (3) may be due to a number of factors. For example, there may be a lesser concentration of sperm outside of the heterogeneous inseminate (3), or the first amount of sperm (14) having greater initial level of fertility (19) may contribute, supplement or afford within the heterogeneous inseminate (3) a physical stimulus or chemical stimulus that acts upon the second amount of sperm (16) to generate the increased level of fertility (20) within the heterogeneous inseminate (3), or the second amount of sperm (16) may exhibit an increased level of motility (60) within the heterogeneous inseminate (3) as compared to outside of the heterogeneous inseminate (3), such greater motility can act to increase fertility of the second amount of sperm (16) in the heterogeneous inseminate (3).

Figure 2:
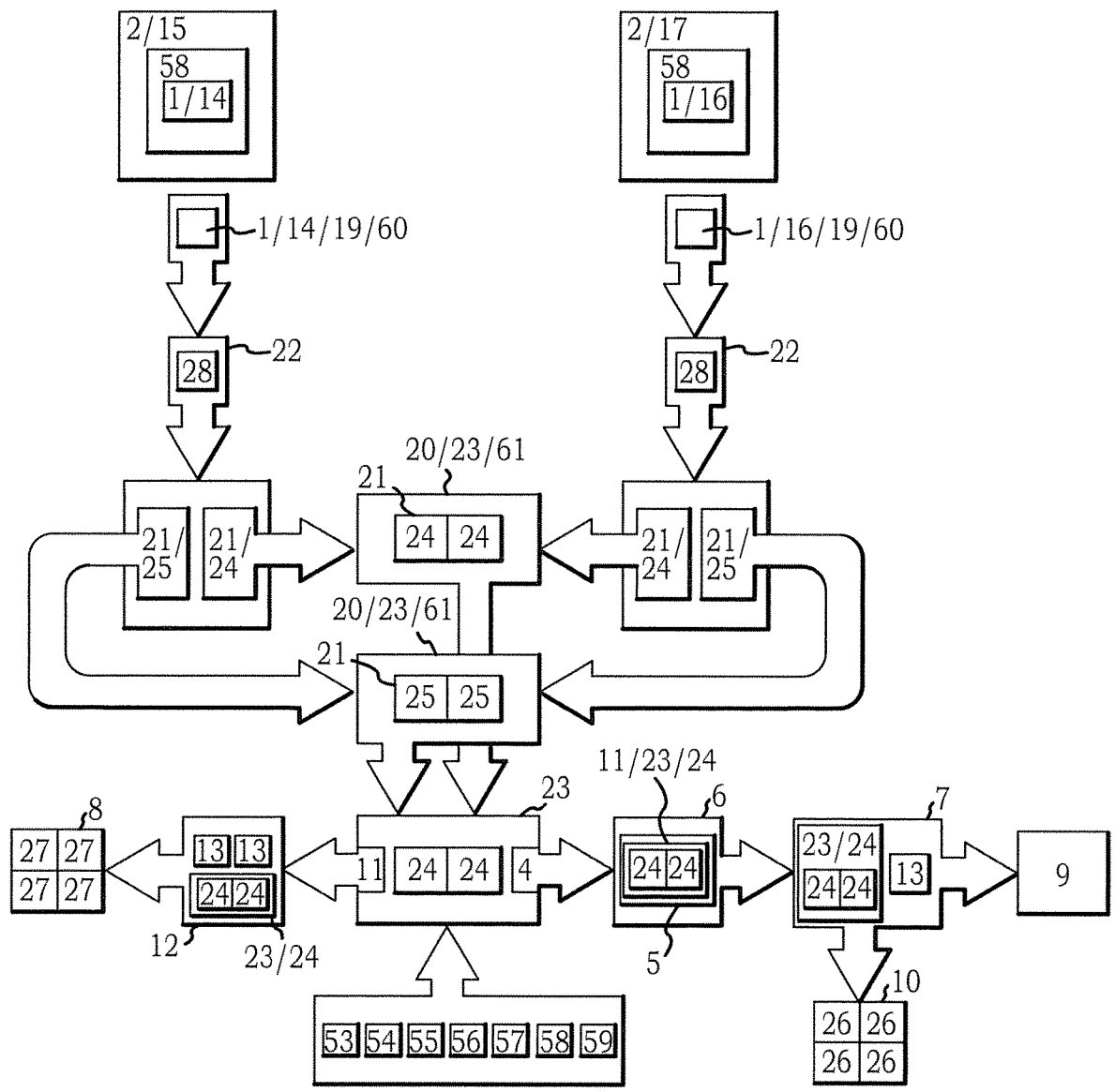
FIG. 2 is a block diagram which shows a particular method of how to make and use an embodiment of the inventive heterogeneous inseminate.

Now referring primarily to FIG. 1 and FIG. 2, embodiments of the heterogeneous inseminate (3) can further include a first amount of sperm (14) and a second amount of sperm (16) (or a plurality of amounts of sperm (1)) from a corresponding first male animal (15) and a second male animal (17) (or plurality of male animals (2)) of the same species in which the first amount of sperm (14) or the second amount of sperm (16) or both the first amount of sperm (14) and the second amount of sperm (16) (or plurality of amounts of sperm (1)) can be sex-selected sperm (21).

Now referring primarily to FIG. 1, as to particular embodiments, the sex-selection process (22) for production of sex-selected sperm (21) can occur after combining the first amount of sperm (14) with the second amount of sperm (16) (or after combining a plurality of amounts of sperm (1)) to achieve the heterogeneous inseminate (3). After combination, the heterogeneous inseminate (3) can then undergo the sex selection process (22) resulting in a sex-selected heterogeneous inseminate (23) containing X-chromosome bearing sperm (24) and a sex-selected heterogeneous inseminate (25) containing Y-chromosome bearing sperm (25). The sex-selected heterogeneous inseminate (23) can contain X-chromosome bearing sperm (24) of the first amount of sperm (14) and the second amount of sperm (16) (or the plurality of amounts of sperm (1)) in similar proportion or concentration as in the original heterogeneous inseminate (3) to afford the substantial advantages above-described.

Similarly, the sex-selected heterogeneous inseminate (23) can contain Y-chromosome bearing sperm (25) of the first amount of sperm (14) and the second amount of sperm (16) (or plurality of amounts of sperm (1)) in similar proportion or concentration to the original heterogeneous inseminate (3) to afford the substantial advantages above-described. The sex-selected heterogeneous inseminate (23) containing X-chromosome bearing sperm (24) or the sex-selected heterogeneous inseminate (23) containing (Y-chromosome bearing sperm (25) can be used in-vitro or in-vivo to fertilize the eggs (13) of a female animal (7) of the same species to produce sex-selected in-vivo embryos (26) and sex-selected offspring (9) or produce sex-selected in-vitro embryos (27) of a pre-selected sex. While FIGS. 1 and 2, show a sex-selected heterogeneous inseminate (23) containing only X-chromosome bearing sperm (24) of two or more male animals (2) being used for in-vivo (6) and in-vivo (12) insemination of eggs (13); the invention is not so limited, and as above described embodiments of the sex-selected homogeneous inseminate (23) can include the X-chromosome bearing sperm (24) of two or more male animals (2) or the Y-chromosome bearing sperm (25) of two or more male animals (2).

Now referring primarily to FIG. 2, as to particular embodiments, the sex-selection process (22) for production of sex-selected sperm (21) can occur prior to combining the first amount of sperm (14) with the second amount of sperm (16) (or prior to combining the plurality of amounts of sperm (1)) to produce a sex-selected heterogeneous inseminate (23). As to these embodiments, each of the first amount of sperm (14) and the second amount of sperm (16) (or the plurality of amounts of sperm (1)) separately undergo the sex selection process (22). The first amount of sperm (14) can be separated into a subpopulation of X-chromosome bearing sperm (24) and into a subpopulation of Y-chromosome bearing sperm (25). Similarly, the second amount of sperm (16) (or each of the plurality of amounts of sperm (1)) can be separated into isolated subpopulations respectively containing X-chromosome bearing sperm (24) and Y-chromosome bearing sperm (25). An amount of the X-chromosome bearing sperm (24) obtained from the first amount of sperm (14) can be combined with an amount of the X-chromosome bearing sperm (24) obtained from the second amount of sperm (16) (or the X-chromosome bearing sperm (24) of a plurality of amounts of sperm (1) can be combined) to provide the sex-selected heterogeneous inseminate (23) containing X-chromosome bearing sperm (24). Similarly, an amount of Y-chromosome bearing sperm (25) obtained from the first amount of sperm (14) can be combined with an amount of the Y-chromosome bearing sperm (25) obtained from the second amount of sperm (16) (or the Y-chromosome bearing sperm of a plurality of amounts of sperm (1) can be combined) to provide a sex-selected heterogeneous inseminate (23) containing Y-chromosome bearing sperm (25).

The amount of the X-chromosome bearing sperm (24) obtained from the first amount of sperm (14) can be adjusted in relation to the amount of the X-chromosome bearing sperm (24) obtained from the second amount of sperm (16) (or the X-chromosome bearing sperm obtained from each of the plurality of amounts of sperm (1) can be adjusted in relation to each other) to achieve a desired concentration or proportion of X-chromosome bearing sperm (24) from the first amount of sperm (14) and the second amount of sperm (16) (or the plurality of amounts of sperm (1)) in the sex-selected heterogeneous inseminate (23) to afford the substantial advantages above-described.

Similarly, the amount of the Y-chromosome bearing sperm (25) obtained from the first amount of sperm (14) can be adjusted in relation to the amount of the Y-chromosome bearing sperm (25) obtained from the second amount of sperm (16) (or the Y-chromosome bearing sperm obtained from each of the plurality of amounts of sperm (1) can be adjusted in relation to each other) to achieve a desired concentration or proportion of Y-chromosome bearing sperm (25) from the first amount of sperm (14) and the second amount of sperm (16) (or the plurality of amounts of sperm (1)) in the sex-selected heterogeneous inseminate (23) to afford the substantial advantages above-described.

The sex-selected heterogeneous inseminate (23) containing X-chromosome bearing sperm (24) or the sex-selected heterogeneous inseminate (23) containing Y-chromosome bearing sperm (25) (or a particular proportion of X-chromosome bearing sperm (24) to Y-chromosome bearing sperm (25)) can be used for in-vitro fertilization (12) or in-vivo artificial insemination (6) to fertilize the eggs (13) of a female animal of the same species to produce in-vivo sex-selected embryos (26) or in-vitro sex-selected embryos (27) of a pre-selected sex.

In regard to the increased level of fertility (20), particular embodiments of the invention can include a first amount of sperm (14) which outside of the heterogeneous inseminate (3) can have an initial level of fertility (19) of zero or nearly zero for a particular application, which can be due to insufficient numbers of sperm, insufficient motility of sperm, or insufficient physical or chemical stimuli which can be afforded within the heterospermic inseminate (3). Accordingly, once the threshold as to numbers of sperm, motility of sperm or the physical or chemical stimuli is achieved within the heterogeneous inseminate (3), the increased level of fertility (20) of the second amount of sperm (16) can be sufficient to allow successful fertilization of an egg (13) of a female animal (7) for that particular application, which would otherwise be unsuccessful or have a lesser fertility rate.

Understandably, the initial level of fertility (19) can be any level of fertility within a particular application, and the increased level of fertility (20) can be a comparable increase of fertility for that particular application. One measure by which initial level of fertility (19) and increased level of fertility (20) can be assessed is by measure of the initial level of motility (60) of the second amount of sperm (16) (or of any of the plurality of amounts of sperm (1)) outside of the heterogeneous inseminate (3) and the increased level of motility (61) of the second amount of sperm (16) (or of any of the plurality of amounts of sperm (1)) within the heterogeneous inseminate (3). As to embodiments of the inventive heterogeneous inseminate (3) or sex-selected heterogeneous inseminate (23) the increase in the motility of the second amount of sperm (16) within the heterogeneous inseminate (3) (or sex-selected heterogeneous inseminate (23)) as compared to outside of the heterogeneous inseminate (3) can be in the range of between about 1% and about 30%. With respect to sex-selected heterogeneous inseminates (23) as one example, the initial level of motility (60) of sex-selected sperm (21) outside of the sex-selected heterogeneous inseminate (23) shortly after separation by a sex-selection process (22), such as flow cytometry, can be at or below 45% as compared to the increased level of motility (61) of a substantially identical sample of sex-selected sperm (21) within the heterogeneous inseminate (3) of about 60% to about 70%.

Figure 3:
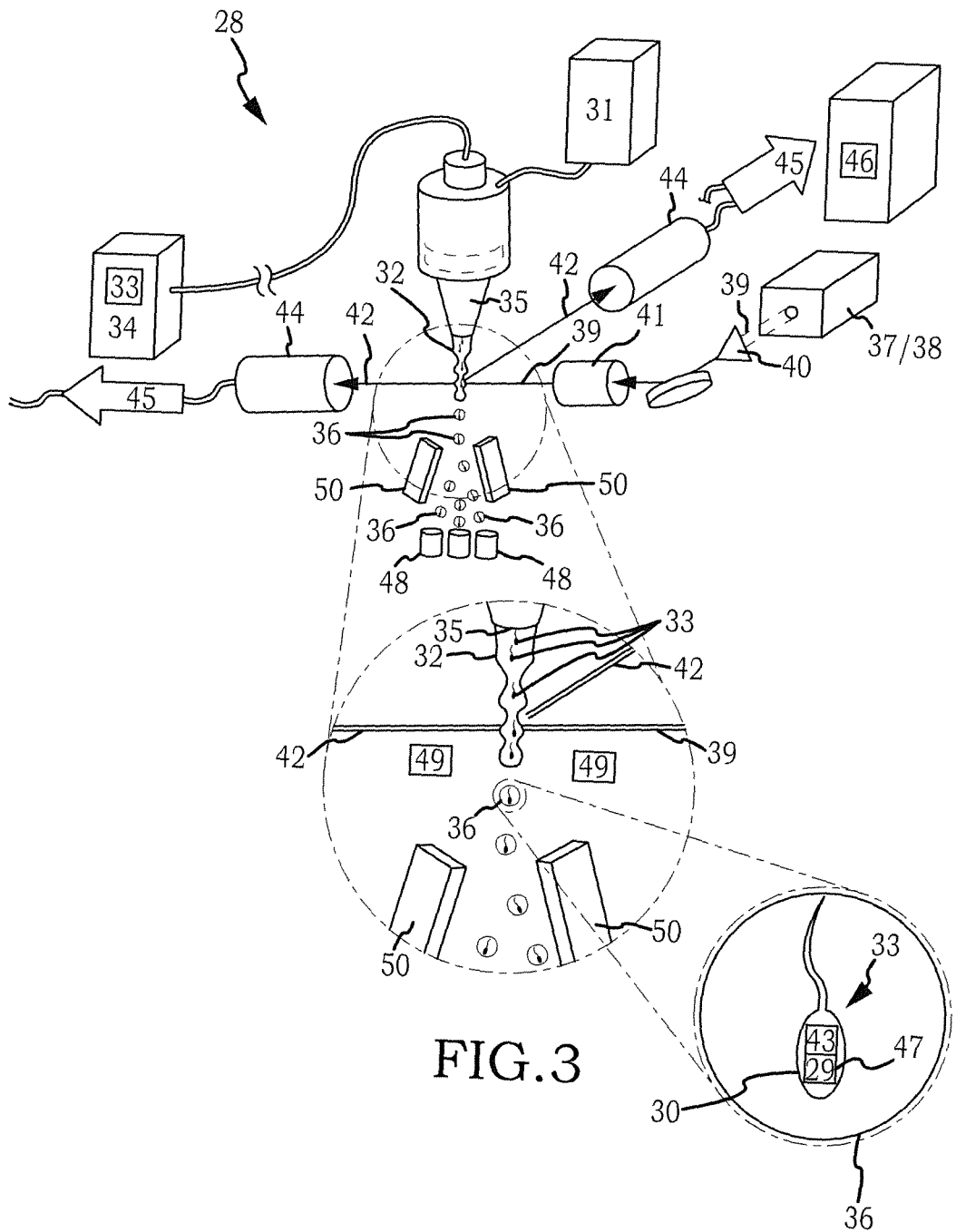
FIG. 3 is an illustration which shows a particular method of producing a sex-selected heterogeneous inseminate by using a flow cytometer in the method shown in FIG. 1 or shown in FIG. 2 to separate X-chromosome hearing sperm cells from Y-chromosome bearing sperm cells.

Now referring primarily to FIG. 3, without limiting the forgoing, a particular process for separating X-chromosome bearing sperm (24) from Y-chromosome bearing sperm (25) is shown. A flow cytometer (28) can be configured to differentiate and the first amount of sperm (14) and the second amount of sperm (16) (where prior combined or separately) based on the amount of deoxyribonucleic acid ("DNA") (29) within the sperm head (30). Typically, a sheath fluid source (31) delivers a fluid stream (32) in which a plurality of sperm cells (33) delivered from a sperm cell source (34) can be entrained. The fluid stream (32) entraining a plurality of sperm cells (33) can be oscillated by a nozzle (35) to generate a plurality of droplets (36) below the nozzle (35). Each of the plurality of droplets (36) can entrain one of the plurality of sperm cells (33). An illumination source (37), such as a laser (38), can emit a beam of light (39), or a plurality of beams of light can be generated by utilizing a plurality of illumination sources (37) or by utilizing a beam splitting element (40) (the beam splitting element shown but not the plurality of beams of light) which can be focused incident upon each of the plurality of sperm cells (33) entrained in the fluid stream (32) below the nozzle (35) through an optical element (41), either as a single beam of light (39) or a plurality of beams of light, whether at the same or different wave lengths. Characteristics of the beam of light (39) can be altered by incidence upon each one of the plurality of sperm cells (33) within the fluid stream (32), or an emission (42) can be generated by incidence of the beam of light (39) upon ligands (43), such as fluorescent materials, or the like, bound to the DNA (29) of each one of the plurality of sperm cells (33). The beam(s) of light (39) having altered characteristics or the emission (42) can be received by a single or a plurality of detectors (44) which can generate a signal (45) for analysis by a computer implemented program (46) to differentiate each one of the plurality of sperm cells (33) correspondingly entrained in each one of the plurality of droplets (36) based upon one or a plurality of sperm cell characteristics (47). Each differentiated one of the plurality of sperm cells (33) can be separated based upon the presence or absence of one or a plurality of the analyzed sperm cell characteristics (47) and collected in a corresponding one of a plurality of collection elements (48). The flow cytometer (28) can further include a droplet charge generator (49) which induces a positive or negative charge in each one of the plurality of droplets (33) and a droplet deflector (50) which acts upon each one of the charged plurality of droplets (36) to establish a trajectory to the proper one of the plurality of collection elements (48). Each of the plurality of collection elements (48) thereby contains a subpopulation of the plurality of sperm cells (33) which can be predominantly X-chromosome bearing sperm (24) or Y-chromosome bearing sperm (25). The purity level (%=100 times the result of X or Y divided by the total of X and Y) of the resulting subpopulation of X-chromosome bearing sperm (24) or the subpopulation of Y-chromosome bearing sperm (25) can exceed 70%, 80%, 90% or can be of even greater purity depending upon the operating parameters of the flow cytometer (28) are adjusted; however, the purity level can be adjusted to be a greater or a lesser percent purity consistent with any particular application. Non-limiting examples of conventional methods of using a flow cytometer (28) to sort the plurality of sperm cells (33) suitable for use in the production of a the heterogeneous inseminate (3) are described in U.S. Pat. Nos. 5,135,759; 6,372,422; 7,195,920 and 7,169,548, each hereby incorporated by reference in the entirety herein; however, the invention is not so limited and any method of producing an enriched subpopulation of X-chromosome bearing sperm (24) or an enriched subpopulation of Y-chromosome bearing sperm (25) can be utilized.

Figure 4:
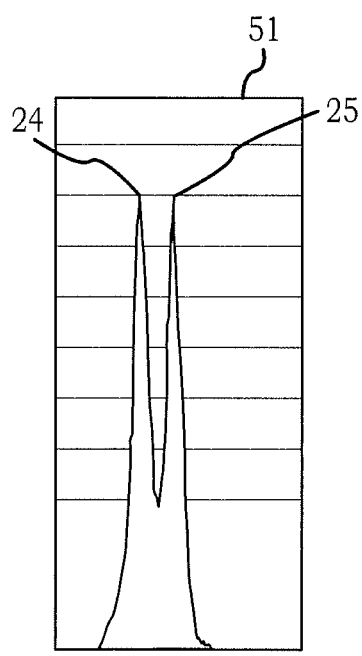
FIG. 4 is a plot which shows the level of resolution achieved between an X-chromosome bearing population and a Y-chromosome bearing population resulting from the separation of sperm in a first amount of sperm obtained from a first male animal using a flow cytometer in accordance with the method shown in FIG. 2.
Figure 5:
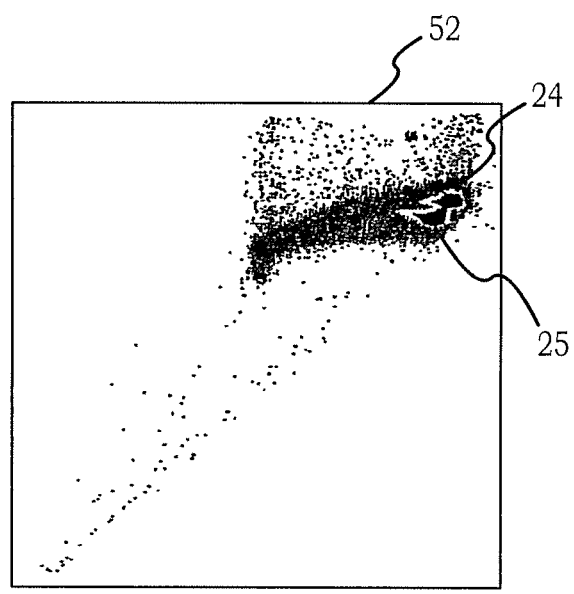
FIG. 5 is a bivariate plot which shows separation of sperm of the first amount of sperm obtained from a first animal separated into an X-chromosome bearing population and a Y-chromosome bearing population using flow cytometer in accordance with the method shown in FIG. 2.

Now referring primarily to FIGS. 2, 4 and 5, a univariate plot (or histogram) (51) (FIG. 4) and a bivariate plot (52) (FIG. 5) can be generated during use of a flow cytometer (28) to separate or sort a first amount of sperm (14) or a second amount of sperm (16) or each of a plurality of amounts of sperm (1) from a corresponding first male animal (15), second male animal (17) or plurality of male animals (2) into subpopulations of X-chromosome bearing sperm (24) and Y-chromosome bearing sperm (25) prior to being combined to achieve an embodiment of the sex-selected heterogeneous inseminate (23) as above described (see also FIG. 2). The histogram (51) (FIG. 4) and the bivariate plot (52) (FIG. 5) show that the mixture of X-chromosome bearing sperm (24) and Y-chromosome bearing sperm (25) in each of a first amount of sperm (14) or second amount of sperm (16) or plurality of amounts of sperm (1) can be resolved into separate corresponding subpopulations of X-chromosome bearing sperm (24) and subpopulations of Y-chromosome bearing sperm (25).

Figure 6:
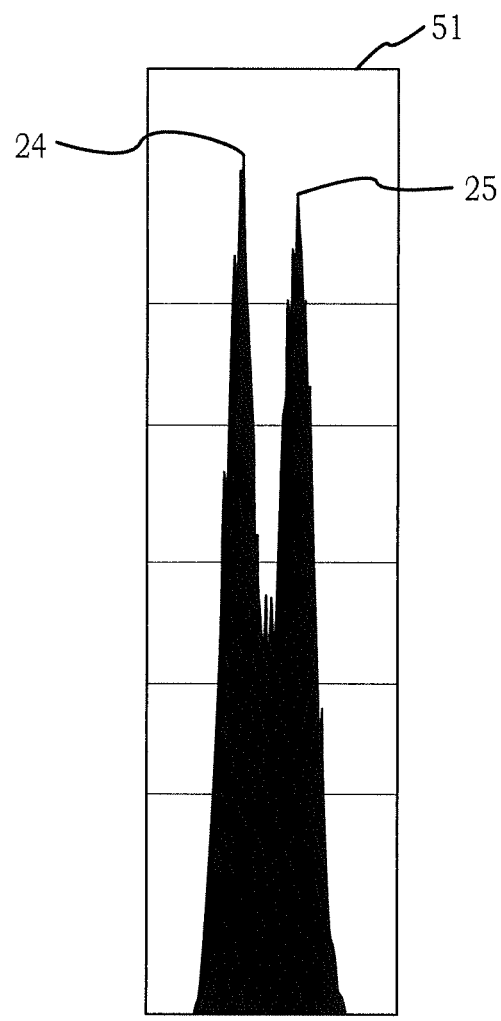
FIG. 6 is a plot which shows the level of resolution achieved between an X-chromosome bearing population and a Y-chromosome bearing population resulting from the separation of sperm of a first amount of spine obtained from a first male animal combined with a second amount of sperm obtained from a second male animal using flow cytometry in accordance with the method shown in FIG. 1.
Figure 7:
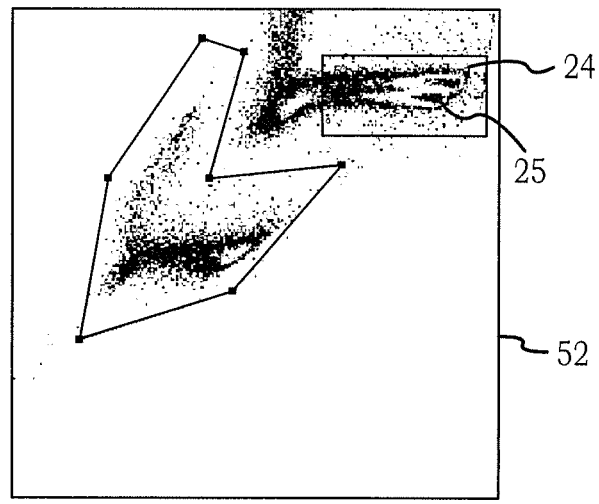
FIG. 7 is a bivariate plot which shows the level of resolution achieved between an X-chromosome bearing population and a Y-chromosome bearing population resulting from the separation of sperm of a first amount of sperm obtained from a first animal combined with a second amount of sperm obtained from a second animal using flow cytometry in accordance with the method shown in FIG. 1.
Figure 8:
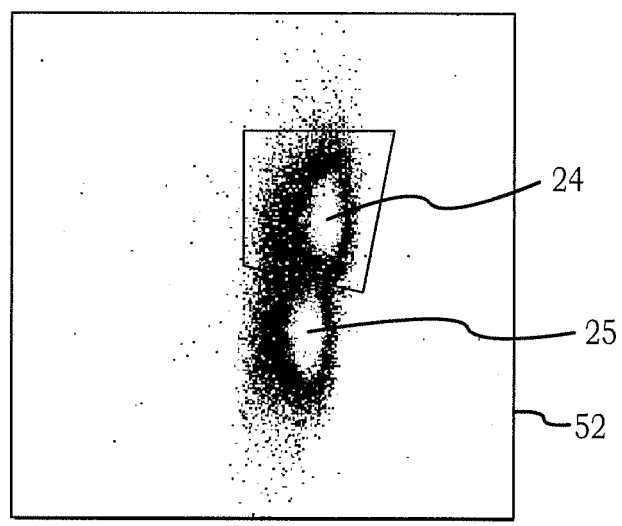
FIG. 8 is an illustration which shows an enlarged portion the bivariate plot shown in FIG. 7.

Now referring primarily to FIGS. 6 through 8, a univariate plot or histogram) (51) (FIG. 6) and bivariate plot (52) (FIG. 7) (see also FIG. 8 showing an enlarged portion of bivariate plot shown in FIG. 7) can be generated during the use of a flow cytometer (28) to separate or sort X-chromosome bearing sperm (24) from Y-chromosome bearing sperm (25) in a heterogeneous inseminate (3) prior achieved by combination of a first amount of sperm (14) with a second amount of sperm (16) or by combination of a plurality of amounts of sperm (1) from a corresponding first animal (15), second animal (17) or plurality of animals (2) of the same species as above described (also refer to FIG. 1). Because of the differences in the same sperm characteristics (47) between a first amount of sperm (14) obtained from a first animal (15) and a second amount of sperm (16) obtained from a second animal (17), or between a plurality of amounts of sperm (1) obtained from a corresponding plurality of animals (2) of the same species, the separation, selection, or sorting (depending upon the method) of the X-chromosome bearing sperm (24) from the Y-chromosome bearing sperm (25) in a heterogeneous inseminate (3) may not have been achieved prior to the instant invention.

For the purposes of this invention, the term "extender" refers to a solution that comes in contact with the plurality of sperm cells (1) or the heterogeneous inseminate (3), or sex-selected sperm (21) or sex-selected heterogeneous inseminate (23), typically for the purpose of dilution or as a cryoprotectant. Typical examples of an extender (53) can contain one or more of: sodium citrate, Tris[hydroxymethyl] aminomethane (also referred to as "TRIS"), TES (N-Tris [Hydroxymethyl]methyl-2-aminoethanesulfonic acid), monosodium glutamate, HEPES medium such as HEPES buffered medium, HEPES buffered bovine gamete medium and particularly HBGM3 and can further contain cryoprotectants such as glycerol, dimethyl sulfoxide, ethylene glycol, propylene glycol; other organic substances such as egg yolk, an egg yolk extract, milk, a milk extract, casein, albumin, lecithin, bovine serum albumin, cholesterol; sugars such as the monosacharides, glucose, fructose, or mannose; detergents such as sodium dodecyl sulfate; antioxidants such butylated hydroxytoluene; capacitation facilitators such as alpha amylase, beta amylase, or beta glucuronidase; antibiotics such as tylosin, gentamicin, lincomycin, spectinomycin, linco-spectin (a combination of lincomycin and spectinomycin), penicillin, streptomycin, and ticarcillin; flow cytometer sheath fluids; and specifically without limiting the forgoing, particular extenders (53) referred to below as TRIS-A (54) and TRIS-B (54); although the inventive heterogeneous inseminate (3) or sex-selected heterogeneous inseminate (23) or methods of using the heterogeneous inseminate (3) or sex-selected heterogeneous inseminate (23) are not limited by the working examples which use TRIS-A (54) or TRIS-B (55) as an extender (53) to dilute concentration of the plurality of sperm cells (1), the sex-selected sperm cells (21) or embodiments of the heterogeneous inseminate (3) or sex-selected heterogeneous inseminate (23) which are diluted by use of TRIS-A (54) or the use TRIS-B (55) as a cryoprotectant (56). The use of TRIS-A (54) or the use of TRIS-B (55) is described in detail as an illustrative example of the numerous and varied extenders that can be used with embodiments of the invention as diluents and cryoprotectants.

For the purposes of this invention the term "TRIS-A" refers to an extender (53) having the formulation in Table 1.

TABLE 1

| TRIS-A Extender. | |
| --- | --- |
| TRIS | 200 mM |
| Citric Acid | 65 mM |
| Fructose | 56 mM |
| Egg Yolk* | 20% by volume |
| Hydrochloric Acid addition to pH 6.8 | |

*Egg Yolk can be clarified by winterization process to remove certain particulates and fats.

The formulation of TRIS-A set out in Table 1 can from application to application of the invention be modified to increase viability or reduce damage to the plurality of sperm cells (1), the heterogeneous inseminates (3) or sex-selected heterogeneous inseminates (23) and the above formulation is provided as a non-limiting example of a numerous and wide variety of similar extenders (53) which are suitable for use in making or using the embodiments of the invention. See also, Yassen, A. M. and Foote, R. H., *Freezability of Bovine Spermatozoa in Tris-Buffered Yolk Extenders Containing Different Levels of Tris, Sodium, Potassium and Calcium Ions*, J. Dairy Science, Vol. 50, No. 6, 887-892 (1966), hereby incorporated by reference in the entirety herein. Extenders (53) in general and specifically the particular extender TRIS-A (54) can further include one or more antibiotics (57) as above described or consistent with animal health regulations of any particular jurisdiction. Also, the description of TRIS-A (54) is not intended to be limiting with respect to the wide variety of extenders (53) which can be utilized in making and using certain embodiments of the invention, as described above.

For the purposes of this invention the term "TRIS-" refers to an extender having the formulation in Table 2.

TABLE 2

| | |
|---|---|
| TRIS | 200 mM |
| Citric Acid | 65 mM |
| Fructose | 56 mM |
| Egg Yolk* | 20% by volume |
| Glycerol | 12% by volume |
| Hydrochloric Acid addition to pH 6.8 | |

*Egg Yolk can be clarified by winterization process to remove certain particulates and fats.

The formulation of TRIS-B set out in Table 2 can from application to application of the invention be modified to increase viability or reduce damage to the plurality of sperm cells (1), the heterogeneous inseminates (3) or sex-selected heterogeneous inseminates (23) and the above formulation is provided as a non-limiting example of a numerous and wide variety of similar extenders (53) which are suitable for use in making or using the embodiments of the invention. Again see for example, Yassen, A. M. and Foote, R. H., *Freezability of Bovine Spermatozoa in Tris-Buffered Yolk Extenders Containing Different Levels of Tris, Sodium, Potassium and Calcium Ions*, J. Dairy Science, Vol. 50, No. 6, 887-892 (1966). Extenders (53) in general and specifically the particular extender TRIS-B (55) can further include one or more antibiotics (57) as above described or consistent with animal health regulations of any particular jurisdiction. Additionally, while TRIS-B (55) of the particular formulation set out in Table 2 uses glycerol as a cryoprotectant (56) the invention is not so limited. Also, the description of TRIS-B is not intended to limiting with respect to the wide variety of extenders (53) which can be utilized in making and using certain embodiments of the invention, as described above.

Again referring primarily to FIGS. 1 and 2, as to particular embodiments, the plurality of sperm cells (1), the first amount of sperm (14) and the second amount of sperm (16) (whether or not sex-selected sperm (21)), the resulting heterogeneous inseminate (3) or sex-selected heterogeneous inseminate (23) can further include an amount of seminal fluid (58), which may be may be cell free semen (59) prepared by removal of entrained sperm (1) which may be diluted with an extender (53). Removal of entrained sperm (1) from the seminal fluid (58) can be achieved by centrifugation of semen at about 500×g for about 15 minutes. The seminal fluid (58) decanted and centrifuged a second time at 500×g for about 15 minutes.

Again referring to FIGS. 1 and 2, embodiments of the homogeneous inseminate (3) or sex-selected homogeneous inseminate (23) can further include a particular dosage form. As one non-limiting example, the dosage form for artificial insemination (6) of cattle can be a one-quarter cubic centimeter (0.25 cc) artificial insemination straw (5) which contains the heterogeneous inseminate (3) or sex-selected heterogeneous inseminate (23). While the Figures only show a sex-selected heterogeneous inseminate (23) contained in the artificial insemination straw (5); the invention is not so limited and dosage forms whether in the form of an artificial insemination straw (5) or otherwise can contain a heterogeneous inseminate (3), a sex-selected heterogeneous inseminate (23), or can contain a combination of both a heterogeneous inseminate (3) and sex-selected heterogeneous inseminate (23).

Again referring to FIGS. 1 and 2, dosage forms of the heterogeneous inseminate (3) and the sex-selected heterogeneous inseminate (23) can be produced by similar steps or procedures as conventional insemination or sex-selected insemination dosage forms; however, the use of the heterogeneous inseminate (3) or sex-selected heterogeneous inseminate (23) can by comparison provide artificial insemination dosages (4) or in-vitro fertilization dosages (11) which exhibit an increased level of motility (61) or have an increased level of fertility (20).

Now referring primarily to FIG. 1, as one non-limiting example, a bovine embodiment of a sex-selected heterogeneous inseminate (23) can be produced by obtaining a first amount of sperm (14) (whether fresh or cryopreserved) of a first male animal (15) and obtaining a second amount of sperm (16) (whether fresh or cryopreserved) of a second male animal (17) of the same species of bovine male animal (or by obtaining a plurality of amounts of sperm (1) from a plurality of male animals (2) of the same species). The first amount of sperm (14), the second amount of sperm (16), or the plurality of amounts of sperm (1) can each be separately suspended in an amount of TRIS-A (54) (or other extender (53)) and then centrifuged in range of about 500 rounds per minute ("rpm") and about 5,000 rpm for a period of time in a range of between about one minute and about ten minutes. The supernatant can be decanted from each of the amounts of sperm (14)(16)(1). Each of the amounts of sperm (14)(16)(1) can be extended with TRIS-A (54) (or other extender (53)) to achieve a concentration which allows each the extended first amount of sperm (14), second amount of sperm (16), or plurality of amounts of sperm (1) to be combined to produce a heterogeneous inseminate (3) each of the first amount of sperm (14), the second amount of sperm (16), or each of a plurality of amounts of sperm (1) at a desired concentration within the heterogeneous inseminate (3).

As a non-limiting example, the concentration of the first amount of sperm (14) and the second amount of sperm (16) within the heterogeneous inseminate (3) can be about 75 million sperm per milliliter. The concentration of the first amount of sperm (14) in the heterogeneous inseminate (3) can be about 55 million sperm per milliliter and the concentration of the second amount of sperm (16) in the heterogeneous inseminate (3) can be about 20 million sperm per milliliter; however the invention is not so limited and the concentration of the first amount of sperm (14) or the second amount of sperm (16) or a plurality of amounts of sperm (1) within the heterogeneous inseminate (3) can be at any predetermined concentration depending upon the application, which as to certain embodiments can provide about equal concentration of each of a plurality of amounts of sperm (1) from a corresponding plurality of animals (2) or can provide unequal concentration as to a plurality of amounts of sperm (1) from a corresponding plurality of animals (2).

The heterogeneous inseminate (3) can then be incubated in about 38 micromolar Hoechst 33342 at about 75 million sperm/ml in the extender (53) for 1 hour at about 34° C.; although other stains or staining conditions can be utilized, to achieve staining of the DNA of the first amount of sperm (14), the second amount of sperm (16), or the plurality of amounts of sperm (1) within the heterogeneous inseminate (3) for separation into subpopulations containing X-chromosome bearing sperm (24) and Y-chromosome bearing sperm (25), as above described or otherwise. As an example, the stained sperm contained in the heterogeneous inseminate (3) can be interrogated by laser excitation at 351 and 364 nm at 150 mW and based on the difference in fluorescent emission be separated into subpopulations of X-chromosome bearing sperm (24) and Y-chromosome bearing sperm (25) using a MOFLO flow cytometer (28) (or other makes or models of flow cytometers or multiple flow channel apparatus). The subpopulations of X chromosome-bearing sperm (24) and Y-chromosome bearing sperm in of about 90% purity as verified by resort analysis can be collected at between about 1,500 live sperm/second and about 5,000 live sperm in/second into 2-ml Eppendorf tubes containing 100 micromolar Cornell Universal Extender (CUE) with 20% egg yolk.

Collected sex-selected sperm (21) can be centrifuged at about 600×g for 10 min and resuspended in TRIS B (55) to a concentration of about 2 million motile sex-selected sperm/ml to provide an embodiment of a sex-selected heterogeneous inseminate (23). The sex-selected heterogeneous inseminate (23) can be cooled to about 5° C. over about 75 minutes and artificial insemination dosages (4) transferred into 0.25-cc artificial insemination straws (5) (about 150 microliters to about 200 microliters per straw). Straws can be cryopreserved, as above described by conventional procedures, or transported at about 3° C. to about 5° C. for use in artificial insemination (6) of female animals (7). Artificial insemination dosages (4) and control dosages can be inseminated using side-opening blue sheaths (IMV), one half of each straw into each uterine horn of female animal (7) of the same bovine species (total of about $3.5 \times 10^5$ sex-selected sperm per artificial insemination dosage or about 250,000 sex-selected sperm from the first amount of sperm (14) and about 50,000 sex-selected sperm from the second amount of sperm (16)). Understandably, the respective concentration of sex-selected sperm (21) in an artificial insemination dosage (4) between a first amount of sperm (14), a second amount of sperm (16), or a plurality of amounts of sperm (1) can be adjusted by adjusting the initial concentration of the sex-selected insemination (23) prior to division into the corresponding plurality of artificial insemination dosages (4) other dosage forms.

Now referring primarily to FIG. 2, as a general non-limiting example, a bovine embodiment of a sex-selected heterogeneous inseminate (23) can be produced by obtaining a first amount of sperm (14) as sex-selected sperm cells (21) (whether fresh or cryopreserved) of a first male animal (15) of a bovine species. The first amount of sperm (14) can be suspended in an amount of TRIS-A (54) (or other extender (53)) and then centrifuged in range of about 500 rounds per minute ("rpm") and about 5,000 rpm for a period in a range of between about one minute and about ten minutes. The supernatant can be decanted. The first amount of sperm (14) can be extended with TRIS-A (54) extender (or other extender (53)) to achieve a concentration of the extended first amount of sperm (14) of about four times greater than the expected concentration of the second amount of sperm (16), or other concentration depending upon the application. The four times concentration of the first amount of sperm (14) in TRIS-A (54) (or other extender (53)) can be for example a concentration in a range of about 3.2 million sperm cells per milliliter and about 128 million sperm cells per milliliter.

The extended first amount of sperm (14) (sex-selected sperm (21)) can be cooled to a temperature in a range of about 4 degrees Celsius ("° C.") and about 5° C. The cooled extended first amount of sperm (14) can be held at this temperature to allow the membranes of the first amount of sperm (14) to move toward equilibrium or equilibrate with the TRIS-A (typically a period of about 90 minutes or as to certain embodiments not less than 90 minutes). The cooled extended first amount of sperm (14) can be held in this condition not to exceed a length of time in which the sperm cells (14) remain viable or capable fertilizing an egg (13) of a female animal (7) of the same species as the first and second male animals (15)(17). Typically, the period of time held will not exceed 12 hours.

A second amount of sperm (16) as sex-selected sperm cells (21) (fresh or cryopreserved) can be obtained of a second male animal (17) of the same bovine species. The second amount of sperm (16) can be suspended in an amount of TRIS-A (54) (or other extender (53)) and then centrifuged in range of about 500 rounds per minute ("rpm") and about 5,000 rpm for a period in a range of between about one minute and about ten minutes. The supernatant can be decanted and the pellet containing the second amount of sperm (16) can be suspended in an amount of TRIS-A (54) to achieve a concentration of the second amount of sperm (16) of about one-fourth that of the first amount of sperm (14). Accordingly, the second amount of spine (16) as a non-limiting example can have a concentration in a range of about 800,000 sperm per milliliter and about 32 million sperm per milliliter depending upon various factors such as the species of the second male animal (17), the scarcity of the sperm, the fertility of the sperm, the dosage form, the method of insemination (whether artificial insemination (6) or in-vitro fertilization (12)), whether for multiple ovulation embryo transfer or single ovulation single embryo production, the female animal (7) of the same species as the first and second male animal (15)(17) being inseminated, or the like.

The extended second amount of sperm (16) can be cooled to a temperature in a range of about 4° C. and about 5° C. The cooled extended second amount of sperm (16) can be held at this temperature to allow the membranes of the second amount of sperm (16) to move toward equilibrium or equilibrate with the TRIS-A (54) (typically a period of about 90 minutes or as to certain embodiments not less than 90 minutes).

About equal volumes of the cooled extended first amount of sperm (14) (sex-selected sperm (21)) and the cooled extended second amount of sperm (16) (sex-selected sperm (21)) can be combined to achieve two times greater concentration of the first amount of sperm (14) with respect to the final concentration of the second amount of sperm (16) contained in the resulting heterogeneous sex-selected inseminate (23).

To the resulting sex-selected heterogeneous inseminate (23) about an equal volume of TRIS-B (55) (containing between about 12% and 20% glycerol) can be added and the combination cooled to temperature in a range of about 4° C. and about 5° C. The cooled extended sex selected heterogeneous inseminate (23) can be held at this temperature to allow the membranes of the sperm cells (1)(21) to move toward equilibrium or equilibrate with the TRIS-B (55) (typically a period in the range of about 30 minutes and about 90 minutes or as to certain embodiments not less than 90 minutes). The cooled sex selected heterogeneous inseminate (23) can be held in this condition not to exceed a length of time in which the sex-selected sperm cells (21) remain viable or capable fertilizing an egg (13) of a female of the same species as the male animals (2).

The cooled sex-selected heterogeneous inseminate (23) can be handled by normal procedures utilized for producing artificial insemination doses (6). Accordingly, as to certain embodiments, the cooled sex selected heterogeneous inseminate (23) can be aliquoted into 0.25 cc artificial insemination straws (5) (about 150 microliters to about 200 microliters per straw). The 0.25 cc artificial insemination straw (5) can contain an amount of the sex-selected heterogeneous inseminate (23) which contains sex-selected sperm (21) from the second amount of sperm (16) in the range of about 50,000 and about 2 million and from the first amount of sperm (14) in the range of about 200,000 and about 8 million. However, a greater or lesser number of the first amount of sperm (14) and the second amount of sperm (16) can be included a 0.25 cc artificial insemination straw (5) by adjusting the initial concentrations of the first amount of sperm (14) and the second amount of sperm (16) with the total number of sperm in each artificial insemination dosage (4) of the instant example being in the range of about 250,000 and about 10 million sex-selected sperm (21).

The sex-selected heterogeneous inseminate (23) can be used for artificial insemination (6) to fertilize the egg(s) (13) of a female animal (7) of the same species as the first and second male (15)(17) for the production of sex-selected in-vivo embryo (26) whether as single embryo pregnancies to generate offspring (9) for meat or animal replacement or multiple embryo pregnancies for MOET by subsequent flushing of a plurality of sex-selected embryos (10). Alternately, the sex-selected heterogeneous inseminate (23) can be used in-vitro fertilization procedures (12) to fertilize eggs (13) of obtained from a female animal (7) of the same species to produce in vitro sex-selected in-vitro fertilized embryos (27).

The use of heterogeneous sex-selected inseminate (23) can result in increased fertility rates. As one non-limiting example, where a plurality of amounts of sperm (1) are processed in accordance with either the method shown in FIG. 1 or FIG. 2 and as described above to produce a sex-selected heterogeneous inseminate (23), the sex-selected heterogeneous inseminate (23) can have an increased level of fertility (20) overall as compared to any initial level of fertility (19) for any one of the plurality of amounts of sperm (1) outside of the sex-selected heterogeneous inseminate (23).

As a second non-limiting example, where a plurality of amounts of sperm (1) from a corresponding plurality animals (2) of the same species are processed as above described to provide a sex-selected heterogeneous inseminate (23) which includes at least one amount of sex-selected sperm (21) having a comparably greater initial level of fertility (19) to one or more amounts of sex-selected sperm (23) having a lesser initial level of fertility (19) outside of the sex-selected heterogeneous inseminate (23), the one or more of the amounts of sex-selected sperm (21) within the sex-selected heterogeneous inseminate (23) will exhibit an increased level of fertility (20) which can exceed the initial level of fertility (19) of the amount of sex-selected sperm having the greater initial level of fertility (19).

As a third non-limiting example, the seminal fluid (58) of one or more amounts of sex-selected sperm (21) which exhibit a comparably greater initial level of fertility (19) outside of the sex-selected heterogeneous inseminate (23) can be stored as an amount of cell free semen (59) and added back into the sex-selected heterogeneous inseminate (23) processed in accordance with either the method shown in FIG. 1 or FIG. 2 and as described above to produce a sex-selected heterogeneous inseminate (23). The amount of cell free semen (59) in a sex-selected heterogeneous inseminate (23) can be in the range of zero cell free semen to about 2 parts cell free semen (59) to one part sex-selected heterogeneous insemination (23). The concentration of the sex-selected sperm (21) can be adjusted as above-described to afford the desired concentration of sex-selected sperm (21) in an artificial insemination dosage (4) or an in-vivo insemination dosage (11).

For the purpose of the present invention, the term "combination or combining or combined" refers to any method of putting two or more materials together. Such methods include, but are not limited to, mixing, commingling, incorporating, intermingling, stirring, integrating, or the like.

For the purposes of the present invention, ranges may be expressed herein as from "about" one particular value to "about" another particular value. When such a range is expressed, another embodiment includes from the one particular value to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Moreover, for the purposes of the present invention, the term "a" or "an" entity refers to one or more of that entity; for example, "a sperm cell" refers to one or more of sperm cells. As such, the terms "a" or "an", "one or more" and "at least one" can be used interchangeably herein unless otherwise indicated. According to the present invention, an isolated material or particle is removed from its natural milieu; however, an isolated material does not necessarily reflect the extent to which the material or particle has been purified.

As can be easily understood from the foregoing, the basic concepts of the present invention may be embodied in a variety of ways. The invention involves numerous and varied embodiments of a reduced dose inseminate (3) and methods of making and using such a reduced dose inseminate (3). As such, the particular embodiments or elements of the invention disclosed by the description or shown in the figures accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "flow sorter" should be understood to encompass disclosure of the act of "flow sorting" whether explicitly discussed or not and, conversely, were there effectively disclosure of the act of "flow sorting", such a disclosure should be understood to encompass disclosure of a "flow sorter" and even a "a means for flow sorting." Such alternative terms for each element or step are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

Thus, the applicant(s) should be understood to claim at least: i) each of the heterogeneous inseminate herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof or to obtain any benefit of reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

In addition, the claims set forth below are intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

We claim:

1. A composition, comprising:
a first amount of sperm of an animal, said first amount of sperm containing X-chromosome bearing sperm cells and Y-chromosome bearing sperm cells; and
a second amount of sperm of said animal, said second amount of sperm comprising an isolated subpopulation of X-chromosome bearing sperm cells or an isolated subpopulation of Y-chromosome bearing sperm cells of said animal, said first amount of sperm of said animal combined with said second amount of sperm of said animal, wherein concentration of said first amount of sperm in said composition is sufficient to increase motility or fertility of said second amount of sperm in said composition.

2. The composition of claim 1, wherein said first amount of sperm has a greater concentration in said composition than said second amount of sperm in said composition.

3. The composition of claim 1, wherein said first amount of sperm comprises infertile sperm.

4. The composition of claim 1, wherein said first amount of sperm or said second amount of sperm comprises frozen-thawed sperm.

5. The composition of claim 1, further comprising admixing an amount of cell free seminal fluid with said first amount of sperm and said second amount of sperm.

6. The composition of claim 1, wherein said animal is selected from the group consisting of: a bovine, an aves, and a fish.

7. The composition of claim 1, wherein said animal comprises a bovine mammal and further comprising establishing a concentration of said second amount of sperm of said animal in said composition at about $2 \times 10^4$ sperm per milliliter to about $4 \times 10^6$ sperm per milliliter.

8. The composition of claim 7, wherein said concentration of said first amount of sperm of said animal in said composition is at about $2 \times 10^7$ sperm per milliliter to about $8 \times 10^7$ sperm per milliliter.

9. The composition of claim 8, further comprising a dosage form of said composition having a volume of about one-quarter milliliter to about one milliliter.

10. The composition of claim 9, further comprising an artificial insemination straw containing said dosage form of said composition.

11. The composition of claim 10, wherein said dosage form of said composition is frozen in said artificial insemination straw.

12. The composition of claim 1, wherein said isolated subpopulation of X-chromosome bearing sperm cells or said isolated subpopulation of Y-chromosome bearing sperm cells of said second amount of sperm has a non-naturally occurring ratio of X-chromosome bearing sperm or Y-chromosome bearing sperm.

13. The composition of claim 12, wherein said first amount of sperm comprises an isolated subpopulation of X-chromosome bearing sperm cells or an isolated subpopulation of Y-chromosome bearing sperm cells.

14. The composition of claim 13, wherein said isolated subpopulation of X-chromosome bearing sperm cells or said isolated subpopulation of Y-chromosome bearing sperm cells of said first amount of sperm and said second amount of sperm each have a non-naturally occurring ratio of X-chromosome bearing sperm or Y-chromosome bearing sperm.

15. The composition of claim 14, wherein said isolated subpopulation of X-chromosome bearing sperm cells or said isolated subpopulation of Y-chromosome bearing sperm cells of said first amount of sperm or said second amount of sperm contain DNA binding an amount of stain.

16. The composition of claim 1, wherein said first amount of sperm comprises only infertile sperm.

\* \* \* \* \*